United States Patent [19]
Gaster et al.

[11] Patent Number: 6,066,644
[45] Date of Patent: May 23, 2000

[54] AZASPIRO DERIVATIVES WITH 5HT$_{1B}$ ACTIVITY

[75] Inventors: Laramie Mary Gaster, Bishop's Stortford; Paul Adrian Wyman, Epping, both of United Kingdom

[73] Assignee: SmithKline Beecham p.l.c., Brentford, United Kingdom

[21] Appl. No.: 09/068,382

[22] PCT Filed: Oct. 23, 1996

[86] PCT No.: PCT/EP96/04657

§ 371 Date: May 8, 1998

§ 102(e) Date: May 8, 1998

[87] PCT Pub. No.: WO97/17350

PCT Pub. Date: May 15, 1997

[30] Foreign Application Priority Data

Nov. 8, 1995 [GB] United Kingdom ............... 9522845

[51] Int. Cl.⁷ ............... A61K 31/435; C07D 471/10; C07D 487/10; C07D 491/10; C07D 495/10
[52] U.S. Cl. ............................. 514/278; 546/17
[58] Field of Search ............... 546/17; 514/278

[56] References Cited

U.S. PATENT DOCUMENTS

| | | | |
|---|---|---|---|
| 5,356,893 | 10/1994 | Bradshaw et al. | 514/227.2 |
| 5,952,325 | 9/1999 | Wayman et al. | 514/212 |
| 5,972,951 | 10/1999 | Gaster | 514/278 |

*Primary Examiner*—Alan L. Rotman
*Attorney, Agent, or Firm*—James M. Kanagy; Charles M. Kinzig

[57] ABSTRACT

Compounds of formula (I) in which B is oxygen, $CR^{17}R^{18}$ or $NR^{19}$ where $R^{17}$, $R^{18}$ and $R^{19}$ are independently hydrogen or $C_{1-6}$alkyl or B is a group $S(O)_b$ where b is 1, 2, or 3; and $R^6$ is a group $—(CH_2)_p—R^{15}$ where $R^{15}$ is $OR^{16}$ or $SR^{16}$ is hydrogen or $C_{1-6}$alkyl or $R^{15}$ is $NR^{10}R^{11}$ where $R^{10}$ and $R^{11}$ are as defined for $R^1$; have been found to exhibit $5TH_{1B}$ antagonist activity.

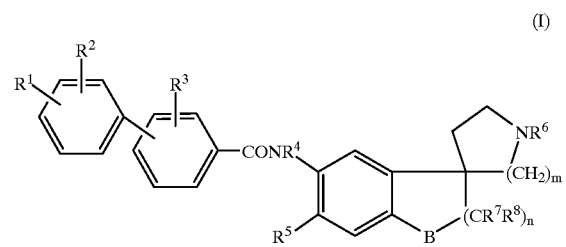

(I)

5 Claims, No Drawings

AZASPIRO DERIVATIVES WITH 5HT$_{1B}$ ACTIVITY

This application is a 371 of PCT/EP96/04657 filed Oct. 23, 1996.

The present invention relates to novel piperidine derivatives, processes for their preparation, and pharmaceutical compositions containing them.

EPA 0 533 266/7/8 disclose a series of benzanilide derivatives which are said to possess 5HT$_{1D}$ receptor antagonist activity. These compounds are said to be of use in the treatment of various CNS disorders. The 5HT$_{1D\beta}$ receptor has now been reclassified as the 5HT$_{1D}$ receptor (P. R Hartig et al Trends in Pharmacological Science, 1996, 17, 103–105.

A structurally distinct class of compounds have now been discovered and have been found to exhibit 5HT$_{1B}$ antagonist activity. In a first aspect, the present invention therefore provides a compound of formula (I) or a salt or N-oxide thereof:

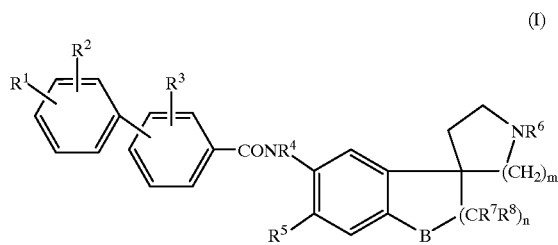

(I)

in which
R$^1$ is an optionally substituted 5 to 7-membered heterocyclic ring containing 1 to 4 heteroatoms selected from oxygen, nitrogen or sulphur;
R$^2$ and R$^3$ are independently hydrogen or C$_{1-6}$alkyl,
R$^4$ is hydrogen or C$_{1-6}$alkyl;
R$^5$ is hydrogen or C$_{1-6}$alkyl or R$^4$ and R$^5$ together form a group —A— where A is (CR$^{13}$R$^{14}$)$_q$ where q is 2, 3 or 4 and R$^{13}$ and R$^{14}$ are independently hydrogen or C$_{1-6}$alkyl or A is (CR$^{13}$R$^{14}$)$_r$—D where r is 0, 1, 2 or 3 and D is oxygen, sulphur or CR$^{13}$=CR$^{14}$;
R$^6$ is a group —(CH$_2$)$_p$—R$^{15}$ where p is 2 and R$^{15}$ is OR$^{16}$ or SR$^{16}$ where R$^{16}$ is hydrogen or C$_{1-6}$alkyl or R$^{15}$ is NR$^{10}$R$^{11}$ where R$^{10}$ and R$^{11}$ are independently hydrogen or C$_{1-6}$alkyl;
R$^7$ and R$^8$ are independently hydrogen or C$_{1-6}$alkyl;
B is oxygen, CR$^{17}$R$^{18}$ or NR$^{19}$ where R$^{17}$, R$^{18}$ and R$^{19}$ are independently hydrogen or C$_{1-6}$alkyl or B is a group S(O)$_b$ where b is 1, 2 or 3;
m is 1, 2 or 3; and
n is 1, 2 or 3.

C$^{1-6}$alkyl groups, whether alone or as part of another group, may be straight chain or branched.

When R$^1$ is a 5 to 7-membered heterocyclic ring containing 1 to 3 heteroatoms selected from oxygen, nitrogen or sulphur suitable heterocyclic rings include thienyl, furyl, pyrrolyl, triazolyl, diazolyl, imidazolyl, oxazolyl, thiazolyl, oxadiazolyl, isothiazolyl, isoxazolyl, thiadiazolyl, pyridyl, pyrimidyl and pyrazinyl. The heterocyclic rings can be linked to the remainder of the molecule via a carbon atom or, when present, a nitrogen atom. Suitable substituents for these rings include R$^2$ and R$^3$ groups as defined above. Preferably R$^1$ is optionally substituted oxadiazolyl. Preferred substituents for such oxadiazolyl groups include C$_{1-6}$alkyl such as methyl or ethyl. Most preferably R$^1$ is a 5-methyl-1,3,4-oxadiazol-2-yl group.

Preferably R$^2$ is C$_{1-6}$alkyl, in particular methyl. Preferably R$^3$ is hydrogen. Suitably R$^4$ is hydrogen or C$_{1-6}$alkyl and R$^5$ is hydrogen or C$_{1-6}$alkyl or R$^4$ and R$^5$ together form a group —A— where A is (CR$^{13}$R$^{14}$)$_q$ where q is 2, 3 or 4 and R$^{13}$ and R$^{14}$ are independently hydrogen or C$_{1-6}$alkyl or A is (CR$^{13}$R$^{14}$)$_r$—D where r is 0, 1, 2 or 3 and D is oxygen, sulphur or CR$^{13}$=CR$^{14}$. Preferably R$^4$ and R$^5$ form a group —A—. Preferably A is (CH$_2$)$_2$. Preferably R$^6$ is a group —(CH$_2$)$_p$—R$^{15}$ where p is 2 and R$^{15}$ is hydroxy. Preferably R$^7$ and R$^8$ are both hydrogen. Preferably m is 2 forming a spiropiperidine ring. Preferably B is oxygen. Preferably n is 1.

Particularly preferred compounds of the invention include:
1'-(2-Hydroxyethyl)-5-(2'-methyl-4'-(5-methyl-1,2,4-oxadiazol-3-yl)biphenyl-4-carbonyl)-2,3,6,7-tetrahydrospiro[furo[2,3-f]indole-3,4'-piperidine],
1'-(2-Hydroxyethyl)-5-(2'-methyl-4'-(5-methyl-1,3,4-oxadiazol-2-yl)biphenyl-4-carbonyl)-2,3,6,7-tetrahydrospiro[furo[2,3 -f]indole-3,4'-piperidine],
1'-(2-Dimethylaminoethyl)-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine],
1'-(2-Methoxyethyl)-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine]or pharmaceutically acceptable salts thereof.

Preferred salts of the compounds of formula (I) are pharmaceutically acceptable salts. These include acid addition salts such as hydrochlorides, hydrobromides, phosphates, acctates, fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Tautomers and mixtures thereof also from an aspect of the invention.

In a further aspect the present invention provides a process for the preparation of a compound of formula (I) which comprises.

(a) reaction of a compound of formula (II):

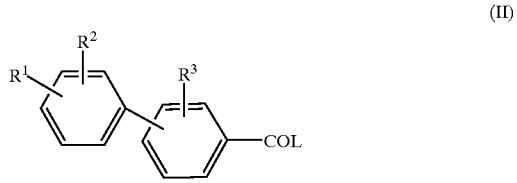

(II)

in which R$^1$, R$^2$ and R$^3$ are as defined in formula (I) and L is a leaving group. with a compound of formula (III):

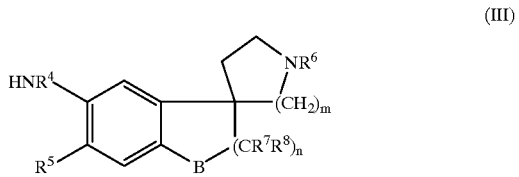

(III)

wherein R$^4$, R$^5$, R$^6$, R$^7$, R$^8$, A, B, m and n are as defined in formula (I); or (b) reacting a compound of formula (IV):

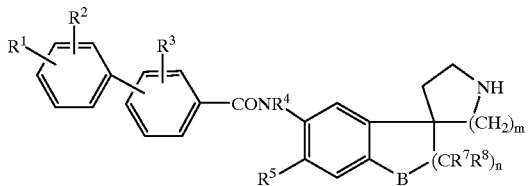

wherein $R^1$, $R^2$, $R^3$, $R^4$, $R^5$, $R^7$, $R^8$, A, B, m and n are as defined in formula (I) with a compound of formula (V):

$$L'—R^6 \qquad (V)$$

where $R^6$ is as defined in formula (I) and L' is a leaving group; and optionally thereafter (a) or (b) in any order:

converting a compound of formula (I) into another compound of formula (I)

forming a pharmaceutically acceptable salt.

Suitable activated carboxylic acid derivatives of formula (II) include acyl halides and acid anhydrides. Activated compounds of formula (II) can also be prepared by reaction of the corresponding carboxylic acid with a coupling reagent such as carbonyldiimidazole, dicyclohexylcarbodiimide or diphenylphosphorylazide. Preferably the group L is halo, particularly chloro.

Compounds of formulae (II) and (III) are typically reacted together in an inert organic solvent such as DMF, THF or dichloromethane at ambient or elevated temperature in the presence of a base such as an alkali metal hydroxide, triethylarnine or pyridine.

Alternatively L is an ester forming group such that the resulting esters of formula (II) can be reacted with compounds of formula (III) in the presence of an organoaluminium reagent such as trimethylaluminium. Such a reaction is typically carried out in the presence of an inert solvent such as toluene.

Intermediate compounds of formulae (II) can be prepared using standard procedures such as those outlined in EPA 533266/7/8. Intermediate compounds of formula (III) can be prepared using standard procedures. Certain intermediate compounds of formula (III) are novel and form a further aspect of the invention.

Reaction of compounds of formulae (IV) and (V) is suitably carried out in the presence of a base in an inert solvent. Preferably L' is a halo, in particular chloro. Preferably the reaction is carried out in an alcoholic solvent at elevated temperature using potassium carbonate as base.

Intermediate compounds of formulae (IV) can be prepared using an analogous coupling procedure to that outlined above for compounds of formulae (II) and (III) using suitable nitrogen protection. Compounds of formula (V) are commercially available or can be prepared using standard procedures.

It will be appreciated to those skilled in the art that it may be necessary to protect certain reactive substituents during some of the above procedures. Standard protection and deprotection techniques can be used. For example, primary amines can be protected as phthalimide, benzyl, benzyloxycarbonyl or trityl derivatives. These groups can be removed by conventional procedures well known in the art.

Carboxylic acid groups can be protected as esters. Aldehyde or ketone groups can be protected as acetals, ketals, thioacetals or thioketals. Deprotection is achieved using standard conditions.

Salts and N-oxides can be prepared using standard procedures. For example N-oxides can be prepared using meta-chloroperoxybenzoic acid or hydrogen peroxide.

$5HT_{1B}$ Antagonists, and in particular the compounds of the present invention, are expected to be of use in the treatment of CNS disorders such as mood disorders, including depression, seasonal effective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; and disorders of eating behaviours, including anorexia nervosa and bulimia nervosa. Other CNS disorders include Parkinson's disease, dementia in Parkinson's disease, neuroleptic-induced Parkinsonism and tardive dyskinesias, as well as other psychiatric disorders.

$5HT_{1B}$ Antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction and hypothermia.

Therefore, the present invention, provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Examples illustrate the preparation of compounds of the invention.

EXAMPLE 1

1'-(2-Hydroxyethyl)-5-(2'-methyl-4'-(5-methyl-1,2,4-oxadiazol-3-yl)biphenyl4-carbonyl)-2,3,6,7-tetrahydrospiro[furo[2,3-f]indole-3,4'-piperidine]

A stirred solution of 5-(2'-methyl-4'-(5-methyl-1,2,4-oxadiazol-3-yl)biphenyl4-carbonyl)-2,3,6,7-tetrahydrospiro[furo[2,3-f]indole-3,4'-piperidine] (E3 in WO 96/19477, 0.44 g, 0.87 mmole) in 2-butanone (30 ml) was treated with potassium carbonate (0.36 g, 2.6 mmole) and 2-chloroethanol (0.18 ml, 2.6 mmole) and heated under reflux for 56 hours, then additional potassium carbonate (0.36 g, 2.6 mmole) and 2-chloroethanol (0.18 ml, 2.6 mmole) added. Reflux was continued for a further 30 hours, then the mixture was concentrated in vacuo and the residue treated with 10% $Na_2CO_3$ solution and extracted with ethyl acetate. The extract was dried, concentrated in vacuo and the residue chromatographed on silica gel eluting with 0–10% methanol/chloroform to afford the title compound as a pale yellow oil (0.18 g, 38%). This was converted to its hydrochloride salt and crystallised from acetone mp. >230° C.

$^1$H NMR (free base) (250 MHz, $CDCl_3$) δ (ppm): 8.15 (s, 1H—low integration), 8.02 (s, 1H), 7.97 (d, 1H), 7.63 (d, 2H), 7.43 (d, 2H), 7.35 (d, 1H), 6.68 (s, 1H), 4.40 (br s, 2H), 4.12 (br t, 2H), 3.65 (br t, 2H), 3.08 (t, 2H), 2.95 (br m, 2H), 2.69 (s, 3H), 2.65–2.50 (m, 3H), 2.36 (s, 3H), 2.30–1.95 (m, 4H), 1.90–1.70 (m, 2H).

EXAMPLE 2

1'-(2-Hydroxyethyl)-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine]

A stirred solution of 5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine] (E17 in WO 96/19477, 1.5 g, 2.9 mmole) in ethanol (30 ml) was treated with sodium carbonate (1.2 g, 11.6 mmole) and 2-bromoethanol (0.41 ml, 5.8 mmole) and heated under reflux for 20 hours. The reaction mixture was concentrated in vacuo and the residue treated with water (10 ml) and extracted with chloroform. The extract was dried ($Na_2SO_4$), concentrated in vacuo and the residue chromatographed on silica gel eluting with 0–6% methanol/chloroform to afford the title compound as a yellow solid (0.9 g, 56%). This was converted to its hydrochloride salt and crystallised from acetone m.p. >250° C.

$^1$H NMR (free base) (250 MHz, $CDCl_3$) δ (ppm): 8.15 (br s, 1H—low integration), 8.00 (d, 1H), 7.92 (dd, 1H), 7.65 (d, 2H), 7.42 (d, 2H), 7.38 (d, 1H), 6.68 (s, 1H), 4.42 (br s, 2H), 4.12 (br m, 2H), 3.65 (br t, 2H), 3.09 (t, 2H), 2.94 (br m, 2H), 2.66 (s, 3H), 2.58 (br t, 2H), 2.38 (s, 3H), 2.25–1.95 (m, 4H), 1.90–1.65 (m, 2H).

EXAMPLE 3

1'-(2-Dimethylaminoethyl)-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine]

A stirred solution of 5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine] (E17 in WO 96/19477, 500 mg, 0.99 mmole) in ethanol (40 ml) was treated with sodium carbonate (419 mg, 3.9 mmole) and 2-dimethylaminoethyl chloride hydrochloride (287 mg, 1.98 mmole) and heated under reflux for 48 hours. The reaction mixture was concentrated in vacuo and the residue treated with 10% $Na_2CO_3$ solution and extracted with ethyl acetate. The extract was dried ($Na_2SO_4$), concentrated in vacuo and the residue chromatographed on silica gel eluting with 0–8% methanol/chloroform to afford the title compound as a yellow/beige solid (75 mg, 13%). This was converted to its hydrochloride salt and crystallised from acetone/ether m.p. 246–248° C.

$^1$H NMR (free base) (250 MHz, $CDCl_3$) δ (ppm): 8.15 (br s, 1H—low integration), 8.00 (d, 1H), 7.91 (dd, 1H), 7.63 (d, 2H), 7.42 (d, 2H), 7.38 (d, 1H), 6.68 (s, 1H), 4.40 (br s, 2H), 4.10 (br s, 2H), 3.08 (t, 2H), 2.96 (br m, 2H), 2.65 (s, 3H), 2.53 (br t, 2H), 2.38 (s, 3H), 2.31 (br s, 6H), 2.15–1.95 (m, 2H), 1.90–1.45 (m, 6H).

EXAMPLE 4

1'-(2-Methoxyethyl)-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine]

The title compound was prepared from 5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine] (E17 in WO 96/19477) and 2-bromoethyl methyl ether using a similar procedure to Example 2, with a reaction time of 31 hours heating under reflux (33%). Hydrochloride salt m.p. 238–240° C.

$^1$H NMR (free base) (250 MHz, CDCl$_3$) δ (ppm): 8.15 (br s, 1H—low integration), 7.98 (d, 1H), 7.91 (dd, 1H), 7.63 (d, 2H), 7.42 (d, 2H), 7.37 (d, 1H), 6.67 (s, 1H), 4.40 (br s, 2H), 4.10 (br m, 2H), 3.54 (br t, 2H), 3.37 (s, 3H), 3.07 (t, 2H), 2.98 (br m, 2H), 2.64 (s, 3H), 2.60 (br t, 2H), 2.37 (s, 3H), 2.25–1.65 (m, 6H).

What is claimed is:

1. A compound of formula (I) or a pharmaceutically acceptable salt or N-oxide thereof:

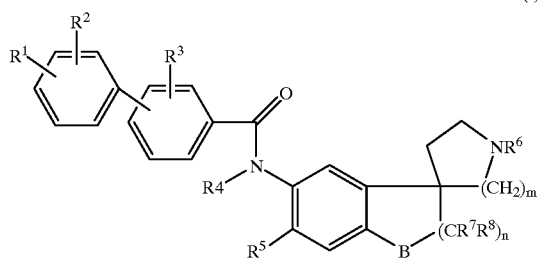

in which $R^1$ is 1,2,4- or 1,3,4-oxadiazole;

$R^2$ and $R^3$ are independently hydrogen or $C_{1-6}$alkyl;

$R^4$ and $R^5$ together form a group —A— where A is $(CR^{13}R^{14})_q$ where q is 2 and $R^{13}$ and $R^{14}$ are hydrogen;

$R^6$ is a group —(CH$_2$)$_p$—$R^{15}$ where p is 2 and $R^{15}$ is OR$^{16}$ or SR$^{16}$ where R$^{16}$ is hydrogen or $C_{1-6}$alkyl or $R^{15}$ is NR$^{10}$R$^{11}$ where R$^{10}$ and R$^{11}$ are independently hydrogen or $C_{1-6}$alkyl;

$R^7$ and $R^8$ are hydrogen;

B is oxygen;

m is 2; and n is 1.

2. A compound according to claim 1 in which $R^2$ is $C_{1-6}$alkyl.

3. A compound according to any one of claim 1 in which $R^6$ is a group (CH$_2$)$_2$OH.

4. A compound according to claim 1 which is:

1'-(2-Hydroxyethyl)-5-(2'-methyl-4'-(5-methyl-1,2,4-oxadiazol-2-yl)biphenyl-4-carbonyl)-2,3,6,7-tetrahydrospiro[furo[2,3-f]indole-3,4'-piperidine], 1'-(2-Hydroxyethyl)-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine], 1'-(2-Dimethylaminoethyl)-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine], 1'-(2-Methoxyethyl)-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine], or a pharmaceutically acceptable salt or N-oxide thereof.

5. A pharmaceutical composition which comprises a compound according to claim 1 in association with a pharmaceutically acceptable carrier or excipient.

* * * * *